United States Patent [19]

Sherrod

[11] Patent Number: 5,145,817
[45] Date of Patent: Sep. 8, 1992

[54] ALKYLATION PROCESS USING DUAL METAL ULTRASTABLE Y ZEOLITE

[75] Inventor: Fred A. Sherrod, Lake Jackson, Tex.

[73] Assignee: The Dow Chemical Company, Midland, Mich.

[21] Appl. No.: 705,450

[22] Filed: May 24, 1991

[51] Int. Cl.⁵ .............................................. B01J 29/08
[52] U.S. Cl. ............................................ 502/65; 502/73
[58] Field of Search ........................ 502/60, 64, 65, 73

[56] References Cited

U.S. PATENT DOCUMENTS

| | | | |
|---|---|---|---|
| 2,904,607 | 9/1959 | Mattox et al. | 260/271 |
| 3,354,077 | 11/1967 | Hansford et al. | 208/111 |
| 3,449,070 | 6/1969 | McDaniel et al. | 23/111 |
| 3,455,842 | 7/1969 | Cornelius et al. | 502/66 |
| 3,508,867 | 4/1970 | Frilette et al. | 502/60 |
| 3,641,177 | 2/1972 | Eberly, Jr. et al. | 260/671 |
| 3,867,307 | 2/1975 | Scherzer et al. | 252/455 |
| 4,219,446 | 8/1980 | Kuehl et al. | 502/65 |
| 4,354,049 | 10/1982 | Ball et al. | 502/60 |
| 4,429,053 | 1/1984 | Ward | 502/65 |
| 4,456,693 | 6/1984 | Welsh | 208/120 |
| 4,701,431 | 10/1987 | Pine | 502/65 |
| 4,891,448 | 4/1990 | Garces et al. | 568/628 |
| 5,004,841 | 4/1991 | Garces et al. | 568/628 |
| 5,015,797 | 5/1991 | Lee et al. | 585/467 |

Primary Examiner—Carl F. Dees

[57] ABSTRACT

A process for the alkylation/transalkylation of benzene is improved by the use of a catalyst prepared by exchanging a sodium Y zeolite with an ammonium salt to replace from about 40 percent to about 90 percent of the sodium ions with ammonium ions; calcining the resulting ammonium-sodium zeolite in steam under conditions sufficient to reduce the unit cell size to about 24.48 to 24.60 angstroms; contacting the calcined catalyst with a rare earth salt and an aluminum salt either simultaneously or sequentially; and calcining the catalyst a second time in the absence of steam.

9 Claims, No Drawings

ALKYLATION PROCESS USING DUAL METAL ULTRASTABLE Y ZEOLITE

BACKGROUND OF THE INVENTION

This invention is related to the liquid-phase alkylation/transalkylation of aromatic hydrocarbons, particularly the alkylation/transalkylation of benzene and substituted benzenes to form ethylbenzene.

Various processing schemes comprising alkylation and/or transalkylation reactions are known to produce monoalkylaromatic products such as ethylbenzene in high yields. However, existing processes are not without problems including the production of undesirable by-products. For example, the production of unwanted xylenes is a particular problem in the production of ethylbenzene in the vapor phase commercial process using ZSM-5 zeolites. Another problem with existing processes concerns the use of Friedel Crafts catalysts such as solid phosphoric acid or aluminum chloride. The phosphoric acid catalysts generally require the use of a water co-feed which produces a corrosive sludge by-product. Problems concerning the sludge by-product can be avoided by the use of zeolite catalysts.

The use of large pore zeolite catalysts in the alkylation of aromatic hydrocarbons is known in the art. Early catalysts were made by simple exchange of the zeolite with a metal salt. For example, U.S. Pat. No. 2,904,607 to Mattox refers to the use of a crystalline metallic aluminosilicate having uniform pore openings of about 6 to 15 angstroms in the alkylation of aromatic hydrocarbons with an olefin. Zeolite alkylation and/or transalkylation catalysts containing a combination of metal and hydrogen sites are well known. U.S. Pat. No. 3,251,897 to Wise describes liquid phase alkylation in type zeolites containing rare earth and hydrogen. Wang et al., *Journal of Catalysis*, 24, 262–271 (1972) describe Y zeolites containing a combination of aluminum and hydrogen that have activity for toluene disproportionation.

Despite these teachings, Type Y zeolites have not been generally used in commercial alkylation of aromatic hydrocarbons, particularly in the production of ethylbenzene. A major problem relating to these catalysts is low activity. An additional problem concerns lack of stability, that is, the loss of crystallinity when a catalyst containing exchanged (i.e. cationic) aluminum and/or hydrogen is exposed to water vapor above 400° C. This means that the catalyst cannot be effectively regenerated. One approach to avoiding this problem is to use a non-metal stabilized Y zeolite. Such catalysts are typically prepared by partial ammonium ion exchange, steam calcination and further ammonium ion exchange. A final heat treatment drives off ammonia gas and leaves an activated hydrogen form of the zeolite. Such catalysts are discussed in U.S. Pat. Nos. 3,449,070 to McDaniel et al.; 3,493,519 to Kerr et al.; 3,293,192 to Maher et al.; 3,354,077 to Hansford; 3,929,672 to Ward; and 3,641,177 to Eberly et al. While these catalysts possess adequate thermal and hydrothermal stability, their catalytic properties are not stable as selectivities decrease significantly with relatively few regeneration cycles, apparently related to the continued shrinkage of the unit cell size.

Thus, Y zeolite catalysts in the hydrogen form are not stable and possess low activity. Rare earth exchanged Y zeolites are stable, but again possess insufficient activity. Non-metal stabilized Type Y zeolites are also stable, but possess selectivities that decline when regenerated. There remains a need for an effective process for the preparation of alkylated aromatics such as ethylbenzene utilizing a stable catalyst having good activity and selectivity.

SUMMARY OF THE INVENTION

The present invention is a process for the preparation of a dual metal ultrastable Y zeolite comprising the following steps:
 (a) contacting a Y zeolite with an ammonium salt to replace from about 40 percent to about 90 percent of the alkali metal ions with ammonium ions;
 (b) calcining the zeolite resulting from step (a) in steam under conditions sufficient to reduce the unit cell size to about 24.48 to about 24.60 angstroms:
 (c) contacting the calcined zeolite of step (b) with a rare earth salt under conditions sufficient to result in the zeolite containing from about 2 to about 5 weight percent of the rare earth:
 (d) calcining the zeolite a second time in the absence of steam following step (c): and
 (e) contacting the zeolite a second time with an aluminum salt to further reduce the alkali metal content to below about 0.3 weight percent.

In the practice of the present invention, steps (c) and (e) may be conducted simultaneously or step (e) may follow step (d).

The present invention also comprises the use of the zeolite prepared as described above in the alkylation of aromatic compounds such as the alkylation of benzene with ethylene to produce ethyl benzene.

The zeolite of the present invention demonstrates good catalytic activity and selectivity levels in the alkylation and transalkylation of aromatic compounds and retains its stability and high selectivity after regenerations. Without wishing to be bound by theory, it is believed that the specified unit cell size contributes to the good selectivity and is stabilized by the rare earth exchange and that the activity level is achieved by the aluminum exchange.

DETAILED DESCRIPTION OF THE ILLUSTRATIVE EMBODIMENTS

The zeolite material used as a starting material herein is faujasite or Type Y zeolite. Such zeolites are well known and have been described, for example in U.S. Pat. 3,130,007. The zeolite has a Si to Al ratio ranging from about 3:1 to about 6:1. Such zeolites may be synthesized by reacting silica, sodium aluminate and caustic in water according to the mole ratio:

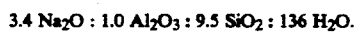

$$3.4\ Na_2O : 1.0\ Al_2O_3 : 9.5\ SiO_2 : 136\ H_2O.$$

Water and caustic are mixed and then a mixture of sodium aluminate, caustic and water is added. The temperature of this material is maintained below about 40° C. and silica is added. This mixture is stirred slowly for 24 hours and the temperature is then increased to about 100° C. and maintained. The Type Y zeolite forms in about 24 to 36 hours. Alternatively, Type Y zeolite may be obtained commercially. The sodium form of Type Y zeolite is typically used although Type Y zeolite with other metal cations may be used. It will be recognized when sodium zeolites are referred to herein, that other metal cations may be substituted for the sodium.

The zeolite is exchanged with an ammonium salt in aqueous solution such that from about 40 to about 90 percent of the sodium ions (or other cations) are replaced with ammonium ions. Examples of ammonium salts that are useful include, for example, nitrate, chloride, sulfate and acetate salts. Since the anion is passive in the ion exchange, its identity is not critical. It is preferred that from about 50 to about 80 percent of the sodium ions are exchanged and more preferred that about 60 to about 70 percent are exchanged. The sodium content is preferably reduced to a range of from about 2.5 to about 6.5 weight percent as $Na_2O$. This exchange may be accomplished using known techniques such as simply heating the zeolite in an aqueous solution of the ammonium salt for one to two hours at 100° C.

The exchanged zeolite is then calcined in the presence of steam. A combination of degree of ammonium exchange, calcination temperature, steam partial pressure and calcination time is selected to result in a reduction of the unit cell size (u.c.s.) of the zeolite to the range of from about 24.48 to about 24.60 angstroms, preferably from about 24.50 to 24.57 angstroms. The specified u.c.s. is critical to the zeolite to the present invention in order to obtain good selectivity.

In a preferred embodiment wherein about 60 to about 70 percent of the sodium ions have been replaced with ammonium ions, calcination temperature is from about 450° to about 600° C., steam partial pressure is from about 10 to 15 psi and the time for calcination is in the range of from about 2 to about 8 hours.

The steam calcined zeolite is then contacted with an aqueous solution of a rare earth salt. By rare earth is meant the elements Y, La, Ce, Pr, Nd, Pm, Sm, Eu, Gd, Tb, Dy, Ho, Er, Tm, Yb and Lu. After this exchange, the zeolite contains from about 2 to about 5 weight percent of the rare earth. This exchange step is conducted at a temperature of from about 25 to about 250° C., more preferably from about 70° to about 100° C. Without wishing to be bound by any theory, it is assumed that the presence of the rare earth ion which is relatively larger than aluminum or hydrogen provides the needed stability to prevent shrinkage of unit cell size when the catalyst is subjected to regeneration.

Following the rare earth exchange, the zeolite is calcined. The temperature of this calcination is preferably from about 400° to about 700° C. for 1 to 10 hours, more preferably at a temperature of from about 500° to 600° C. for about 2 to 5 hours. It is also preferred that this calcination step is conducted in a purge of dry air or nitrogen. Without wishing to be bound by theory, it is believed that this calcination drives the rare earth into zeolitic sites which are optimum for unit cell size stabilization.

After this calcination, the zeolite is contacted with an aqueous solution of an aluminum salt, so that the final sodium content of the zeolite is reduced below about 0.3, more preferably about 0.15 weight percent. In an alternative embodiment, the aluminum and rare earth exchange is performed simultaneously followed by the calcination. Due to the acidic nature of the aluminum salt, some cationic hydrogen is exchanged simultaneously with the aluminum. The combination of aluminum and hydrogen is believed to contribute significantly to the activity and selectivity exhibited by the catalyst of the present invention.

The zeolite catalyst may be used in combination with a support or binder material such as, for example, a porous inorganic oxide support or a clay binder. Nonlimiting examples of such materials include alumina, zirconia, silica, magnesia, thoria, titaria, boria, beryllia, chromia and combinations thereof. Suitable clay materials include bentonite and kieselguhr. The relative proporation of zeolite can be between about 1 and 99 weight percent, more preferably between 10 and 95 weight percent. The binder or support may be added at any stage of the catalyst preparation. In a preferred embodiment, the initial NaY zeolite is mixed with the binder or support to produce tablets or extrudates through conventional procedures. The ion exchanges can then be carried out by pumping the exchange salts through a bed of the tablets or extrudates to effect the exchange.

The preparation of the zeolite catalyst of the present invention may comprise, consist essentially of or consist of the steps described above. It will also be recognized that the dual metal ultrastabilized zeolite of the present invention may be prepared in the absence of any additional elements not specifically mentioned above.

Hydrocarbons which are alkylated or transalkylated by the process of the present invention include aromatic compounds such as benzene, napthalene and anthracene and substituted versions thereof. Examples of substituents include lower alkyl, tertiarybutyl, cycloalkyl, phenyl and napthyl. In a preferred embodiment, benzene is alkylated, and substituted benzenes are transalkylated, to produce ethylbenzene.

Alkylating agents include $C_{2-24}$ alkenes, $C_{1-24}$ alkyl halides, $C_{1-24}$ alcohols and formaldehyde. Preferred alkylating agents include ethylene, propylene and dodecylene with ethylene being more preferred.

As will be recognized by one skilled in the art, operating conditions employed in the process of the present invention are critical and will depend, to a great extent, on the particular alkylation reaction being effected.

In a preferred embodiment wherein benzene or substituted benzene is the aromatic hydrocarbon to be alkylated, the ratio of the benzene or substituted benzene to catalyst may be any weight ratio which produces the desired alkylated benzene with a relatively high selectivity and a low level of impurities. Preferred ratios will also be dependent on the reactor configuration. For example, in batch reactors, the weight ratio of benzene or substituted benzene to catalyst is preferably in the range from about 0.1:1 to about 2000:1. More preferably, the weight ratio is in the range from about 10:1 to about 500:1. Most preferably, the ratio is in the range from about 50:1 to about 100:1. Below the preferred lower limit of 0.1:1, the productivity will be very low. Above the preferred upper limit of 2000:1, the conversion of the aromatic compound may be low.

The ratio of benzene or substituted benzene to alkylating agent may vary depending on the identity of the alkylating agent, type of reaction such as batch or continuous and reaction conditions such as temperature, pressure and weight hourly space velocity (WHSV). When the alkylating agent is ethylene, the ratio of benzene to ethylene is preferably from about 10:1 to about 3:1 in a continuous reactor. As is recognized by one skilled in the art, when different reactor configurations are used, different ratios of reactants may be preferred.

The alkylating agent may be introduced to the reaction all at once, as in the case of a liquid alkylating reagent. Alternatively, the alkylating agent may be introduced to the reaction on demand until the desired degree of conversion is achieved, as in the case of a gaseous alkylating agent which is continuously fed into the reactor.

The contacting of the benzene or substituted benzene with the alkylating agent in the presence of the catalyst may occur in a reactor of any configuration. Batch-type and continuous reactors, such as fixed bed, slurry bed, fluidized bed, catalytic distillation, or countercurrent reactors, are suitable configurations for the contact. Preferably, the reactor is fit with a means for observing and controlling the temperature of the reaction, a means for observing and measuring the pressure of the reaction, and optionally a means for agitating the reactants. The benzene or substituted benzene may be in the liquid form or in solution. The alkylating agent may be introduced in the liquid or gaseous state, and may be added all at once at the start of the reaction, or fed continuously on demand from the reaction. The catalyst may be used in various forms, such as a fixed bed, moving bed, fluidized bed, in suspension in the liquid reaction mixture, or in a reactive distillation column.

The contacting of the reactants in the presence of the catalyst may occur at any temperature or pressure which will produce the desired alkylated products. In the production of ethylbenzene, the temperature is preferably in the range from about 100° C. to about 300° C., more preferably about 180° C. to 250° C. Below the preferred lower limit of 100° C. the reaction proceeds slowly. Above the preferred upper limit of 300° C., the impurity level increases.

The pressure in the reactor is preferably in the range where the aromatic compound to be alkylated is maintained in the liquid phase. When benzene is the aromatic compound, the pressure is generally in the range of from about 500 psig to about 1000 psig to keep benzene in the liquid phase at reactor conditions. Below the preferred lower limit of about 500 psig, the benzene is in the vapor phase and time between regenerations cycles is substantially decreased.

The benzene, alkylating agent and/or transalkylating agent and catalyst are contacted for a time sufficient to convert the benzene to alkylated products, and sufficient to produce the desired yield of product. Generally, the contact time will depend on other reaction conditions, such as temperature, pressure and reagent-/catalyst ratios.

Following the alkylation/transalkylation of the benzene or substituted benzene, the product mixture may be separated by standard techniques.

In a preferred embodiment of this invention, benzene is alkylated with ethylene in the liquid phase by contact in a reaction zone with the rare earth/aluminum containing ultrastable Y zeolite catalyst described above under alkylation and/or transalkylation conditions sufficient to produce ethylbenzene.

The following examples are given to illustrate the catalyst and the process of this invention and should not be construed as limiting its scope. All percentages in the examples are mole percent unless otherwise indicated.

EXAMPLE 1

Catalyst Preparation

A commercially available ⅛ inch extrudate of a sodium form of Type Y zeolite bonded with 20 weight percent acid-washed inorganic oxide is used as the starting material. The extrudates are exchanged with aqueous ammonium chloride to replace 67 percent of the sodium with ammonium ions.

A 380 gram portion of the extrudates are loaded into a tubular reactor and calcined at 550° C. for six hours. Steam at one atmosphere pressure is maintained by pumping water into the top of the reactor at about 0.5 ml/minutes. Excess water is allowed to drain out the bottom of the reactor through a water trap.

The zeolite is cooled and then 8 liters of 0.25 M cerium nitrate are pumped over the zeolite at about 33 ml/minute. This exchange is carried out at 90° C. in a liquid-full vessel. Excess salt is flushed out with water. The cerium exchanged ultrastable Y zeolite is for about fifteen hours at 220° C. in dry nitrogen. The bed temperature is then increased to 510° C. and held for three hours under nitrogen flow. The bed is cooled and the zeolite is re-hydrated by passing water saturated nitrogen over the bed for about six hours.

Eight liters of 0.25 M aluminum chloride is then pumped over the zeolite bed at about 33 ml/minute. This exchange is carried out at 90° C. in a liquid-full vessel. Excess salt is flushed out with water and the catalyst is oven dried at 100° C.

EXAMPLE 2

Catalyst Preparation

The procedure outlined in Example 1 is followed with the exception that 8 liters of a mixture of cerium nitrate (0.125 molar) and aluminum chloride (0.125 molar) are pumped over the zeolite at a rate of about 33 ml/minute rather than having the cerium and aluminum exchanges being conducted sequentially. The remainder of the catalyst preparation is not changed.

EXAMPLE 3

Alkylation of Benzene with Ethylene

Sixty milliliters of the catalyst prepared in Example 1 are loaded into a one inch diameter stainless steel reactor and dried overnight at 200° C. in a flow of dry nitrogen. The bed temperature is then increased to 500° C. and held for three hours while maintaining nitrogen flow. The bed is then cooled and benzene is pumped over the catalyst at 360 ml/hour. A backpressure of about 500 psig is maintained while the reactor temperature is increased to about 200° C. Ethylene is then added at a rate so as to produce an epsilon of 0.21 (epsilon is defined as the total moles of ethyl groups divided by the total moles of benzene rings). The temperature is adjusted to keep the ethylbenzene concentration at about 19 weight percent. The reactor is operated continuously for six days and the benzene feed rate is then reduced to 180 ml/minute and the ethylene feed rate is decreased to maintain an epsilon of 0.21. A maximum reactor temperature of 254° C. was required to obtain a 19 weight percent ethylbenzene concentration. The reactor is operated continuously an additional six days during which the ethylbenzene concentration remained at 19 weight percent with a temperature increase of 2° C. to 256° C.

EXAMPLE 4

Two-stage Alkylation of Benzene with Ethylene

Using the general procedure outlined in Example 3, benzene is alkylated with ethylene at an epsilon of 0.15. The product so obtained is then passed at 180 ml/hour over a 60 ml bed of the catalyst which had been regenerated eleven times by standard burn off in air. The backpressure is maintained at about 500 psig. The temperature is slowly increased to keep the ethylbenzene concentration about 26 percent. The reactor is operated continuously for 27 days during which the reactor temperature is increased from 217° C. to 279° C.

EXAMPLE 5

Two-stage Alkylation of Benzene with Ethylene

Using the general procedure outlined in Example 4, benzene is alkylated with ethylene at an epsilon of 0.21. The product so obtained is then passed at 180 ml/hour over a 60 ml bed of the catalyst which had been regenerated ten times by standard burn off in air. The backpressure is maintained at about 500 psig. The temperature is slowly increased to keep the ethylbenzene concentration about 30 percent. The reactor is operated continuously for 24 days during which the reactor temperature is increased from 223° C. to 301° C.

What is claimed is:

1. A process for the preparation of a dual metal ultrastable Y zeolite comprising the following steps:
   (a) contacting a Y zeolite with an ammonium salt to replace from about 40 percent to about 90 percent of the alkali metal ions with ammonium ions:
   (b) calcining the zeolite resulting from step (a) in steam under conditions sufficient to reduce the unit cell size to about 24.48 to about 24.60 angstroms;
   (c) contacting the calcined zeolite of step (b) with a rare earth salt under conditions sufficient to result in the zeolite containing from about 2 to about 5 weight percent of the rare earth:
   (d) calcining the zeolite a second time in the absence of steam following step (c): and
   (e) contacting the zeolite a second time with an aluminum salt to further reduce the alkali metal content to below about 0.3 weight percent.

2. The process of claim 1 wherein, in step (a), about 60 to about 70 percent of the alkali metal ions are exchanged with ammonium ions.

3. The process of claim 1 wherein steps (c) and (e) are conducted simultaneously, followed by step (d).

4. The process of claim 1 wherein the unit cell size is reduced to about 24.50 to 24.57 angstroms in step (b).

5. The process of claim 1 wherein the alkali metal content is reduced below 0.15 in step (e).

6. The process of claim 1 wherein the rare earth salt used in step (c) is a salt of cerium.

7. The process of claim 1 wherein the alkali metal is sodium.

8. A dual metal ultrastable alkali metal Y zeolite prepared by a method comprising the following steps:
   (a) contacting a Y zeolite with an ammonium salt to replace from about 40 percent to about 90 percent of the alkali metal ions with ammonium ions:
   (b) calcining the zeolite resulting from step (a) in steam under conditions sufficient to reduce the unit cell size to about 24.48 to about 24.60 angstroms:
   (c) contacting the calcined zeolite of step (b) with a rare earth salt under conditions sufficient to result in the zeolite containing from about 2 to about 5 weight percent of the rare earth:
   (d) calcining the zeolite a second time in the absence of steam following step (c): and
   (e) contacting the zeolite a second time with an aluminum salt to further reduce the alkali metal content to below about 0.3 weight percent.

9. The process of claim 1 wherein in step (d), the calcining is done at a temperature of 40° to 700° C.

* * * * *

UNITED STATES PATENT AND TRADEMARK OFFICE
CERTIFICATE OF CORRECTION

PATENT NO. : 5,145,817

DATED : September 8, 1992

INVENTOR(S) : Fred A. Sherrod

It is certified that error appears in the above-identified patent and that said Letters Patent is hereby corrected as shown below:

Column 8, line 35, "40°" should read --400°--.

Signed and Sealed this

Fifth Day of July, 1994

Attest:

BRUCE LEHMAN

Attesting Officer

Commissioner of Patents and Trademarks